United States Patent [19]
Yavitz

[11] Patent Number: 5,740,550
[45] Date of Patent: Apr. 21, 1998

[54] MEMBRANE SHIELD FOR EYES

[76] Inventor: Edward Q. Yavitz, 3828 Spring Creek Rd., Rockford, Ill. 61114

[21] Appl. No.: 867,122

[22] Filed: Jun. 2, 1997

Related U.S. Application Data

[60] Provisional application No. 60/013,479, Mar. 15, 1996.

Related U.S. Application Data

[63] Continuation-in-part of Ser. No. 709,473, Sep. 5, 1996, abandoned.

[51] Int. Cl.[6] .................................................. A61F 9/04
[52] U.S. Cl. ........................................... 2/15; 128/858
[58] Field of Search ......................... 2/15, 11, 426, 2/440, 442, 206; 128/858, 857, 887, 888; 604/294, 295, 300, 301, 302; 602/52, 54, 74; 351/62, 178, 41, 110

[56] References Cited

U.S. PATENT DOCUMENTS

| | | | |
|---|---|---|---|
| 2,143,856 | 1/1939 | Biggs | 2/440 |
| 2,896,615 | 7/1959 | Szigeti | 128/858 |
| 3,068,863 | 12/1962 | Bowman | 128/858 |
| 3,092,103 | 6/1963 | Mower | 128/858 |
| 3,300,786 | 1/1967 | Rosenvold et al. | 128/858 |
| 3,952,735 | 4/1976 | Wirtschafter et al. | 128/163 |
| 3,973,561 | 8/1976 | Kane | 128/858 |
| 4,473,370 | 9/1984 | Weiss | 604/402 |
| 4,682,371 | 7/1987 | Heltman | 2/15 |
| 4,709,695 | 12/1987 | Kohn et al. | 128/858 |
| 4,793,003 | 12/1988 | Riedel et al. | 2/15 |
| 4,862,902 | 9/1989 | Goffman | 2/15 |
| 4,867,146 | 9/1989 | Krupnick et al. | 2/15 |
| 4,969,472 | 11/1990 | Langley et al. | 2/15 |
| 4,979,811 | 12/1990 | Boyer | 2/15 |
| 5,661,850 | 9/1997 | Martinique | 2/15 |

OTHER PUBLICATIONS

Brochure, Pro–ophta™ Adhesive Eye Dressing, Type S, No. 95574.

*Primary Examiner*—Amy B. Vanatta
*Attorney, Agent, or Firm*—Robert A. Van Someren

[57] ABSTRACT

The membrane shield is applied over the eye of a wearer to retain moisture. The moisture shield includes a window that can be made of a transparent plastic. A base rim having a collar is sealingly attached to the perimeter of the window such that the collar extends outwardly from the window. An adhesive layer, such as an adhesive gel, is applied to the collar to permit the moisture shield to be adhered to the wearer's face about the eye.

20 Claims, 2 Drawing Sheets

MEMBRANE SHIELD FOR EYES

This document is a continuation-in-part of the patent application Ser. No. 08/709,473, entitled Membrane Shield for Eyes, filed on Sep. 5, 1996, now abandoned which was based on and claimed priority of Provisional Application No. 60/013,479 entitled Membrane Shield for Eyes, filed on Mar. 15, 1996.

FIELD OF THE INVENTION

The present invention relates generally to a device for protecting mammalian eyes, and particularly to a membrane shield that may be adhered to the face of a person about the eye to retain moisture in the eye

BACKGROUND OF THE INVENTION

When eyes are exposed to the elements, such as heat, cold or dry air, the moisture in the membranes of the eyes tends to evaporate, leaving the person with uncomfortably dry eyes. Retaining moisture is particularly difficult for the elderly and for persons with certain eye disorders. Additionally, it is often helpful to retain a high level of moisture in the membranes of the eyes following certain types of eye surgeries.

Eyes also are susceptible to dirt, bacteria, and other particles that become lodged therein. Dirt and bacteria are especially problematic following certain eye surgeries. They are also a problem in environments where the air is recirculated, as for example, in airplanes.

Standard goggles are currently used to protect the eyes. Goggles are secured over the eyes by a strap that wraps around the wearers head. If the strap is too loose, the goggles will not stay in place. On the other hand, if the strap is tightly fastened, the user may complain that the goggles are uncomfortable. Another problem with goggles is their bulk which makes them conspicuous when worn. Because they take up more space, bulky goggles are also difficult to store in a purse or a pocket.

Another product sold to protect eyes, as well as to treat dry eyes, is the Pro-Ophtha S™, product no. 95574 distributed by Visitec Company, located in Sarasota, Fla. This product has a clear, hard plastic center with a porous flap extending outwardly from the hard plastic center. The porous flap includes an adhesive applied to one surface to permit adherence of the flap to the face of a wearer surrounding one of the wearer's eyes. Due to the porous, vapor permeable nature of the flap, moisture, e.g., water vapor, can still escape from the region surrounding the wearer's eye, and bacteria has access to the eye. For serious dryness problems and for proper therapy following certain eye surgeries, the eye should be separated from the environment by a moisture barrier.

Another product that has been distributed by Solan Opthalmic Products of Jacksonville, Fla. is the Guibor Expo Bandage® Eye Bubble which includes a clear, stiff plastic bubble surrounded by a plastic flap. The flap includes adhesive applied to one surface to permit the product to be adhered over the wearer's eye. However, the bubble is inflexible and the flap is relatively narrow which can lead to gaps between the flap and the wearer's face, thereby providing a less secure moisture barrier.

Both of the above-described products work well for some procedures, but in many applications, it would be advantageous to create a more secure moisture barrier. In other situations, it would be advantageous to have a completely flexible eye covering, and in still other situations, it would be advantageous to incorporate vision correction lenses into the eye shield.

The present invention addresses the drawbacks of existing eye protection devices.

SUMMARY OF THE INVENTION

The present invention, according to a preferred embodiment, features a moisture shield for application to a mammalian face to retain moisture in a mammalian eye. The moisture shield includes a window having a perimeter region. A base is sealingly attached to the perimeter region and includes a flexible collar extending outwardly from the perimeter region. The window and the flexible collar are impermeable to the flow of water vapor therethrough. Additionally, an adhesive layer is disposed on the flexible collar to permit attachment of the moisture shield to the mammalian face about the mammalian eye. According to one aspect of the present invention, the window may be formed as a lens to improve the vision of the wearer. According to other aspects of the invention, the window may be made of a flexible plastic material, such as plastic film, and the adhesive layer may comprise a gel, such as petroleum jelly.

According to another aspect of the invention, a method is provided for making a moisture shield to cover an eye of a mammal, such as a human. The method comprises the steps of forming a window form a moisture impermeable material and combining a moisture impermeable collar with the window. The moisture impermeable collar is designed to extend outwardly from the window. Additionally, the method includes the step of applying a gel to the collar to permit adhering of the collar to the mammal about the eye for a more secure moisture barrier.

Other principle features and advantages of the invention will become apparent to those skilled in the art upon review of the following drawings and detailed description.

BRIEF DESCRIPTION OF THE DRAWINGS

The invention will hereafter be described with reference to the accompanying drawings, wherein like reference numerals denote like elements.

DETAILED DESCRIPTION OF THE PREFERRED EMBODIMENT

Figure 1:
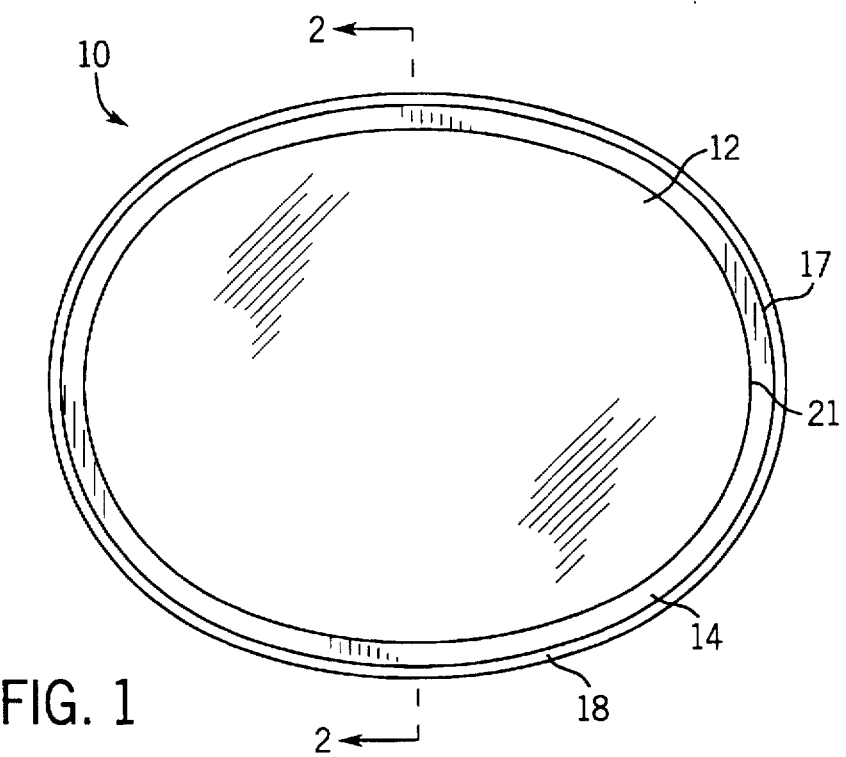
FIG. 1 is a front view of a membrane shield, according to a preferred embodiment of the invention.
Figure 2:
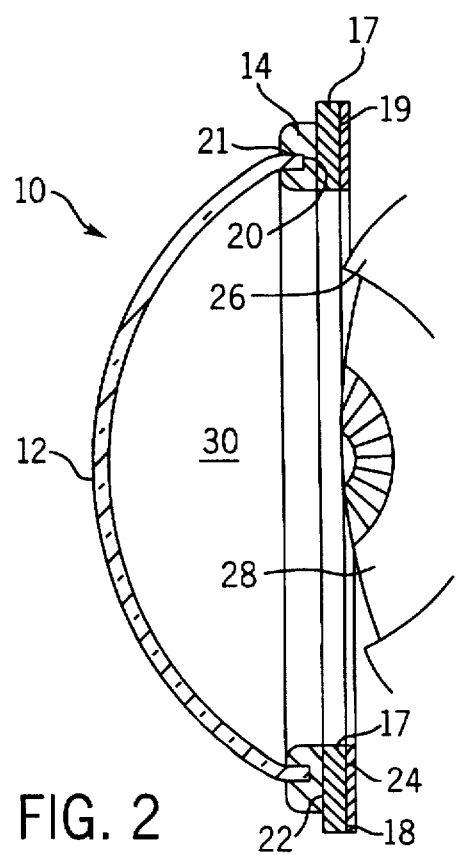
FIG. 2 is a cross sectional view taken generally along line 2—2 of FIG. 1

Referring to FIGS. 1 and 2, membrane shield 10, according to a preferred embodiment of the invention, is illustrated. Membrane shield 10 is designed to protect the eye from dehydration and from particles such as dust and bacteria. Membrane shield 10 includes a central window 12, a base 14, a collar 17 adjoining base 14 and an adhesive 18 for attaching membrane shield 10 to the face of a mammal, such as a human. Additionally, a removable backing 19, such as a wax paper backing, is adhered by adhesive 18 until membrane shield 10 is ready for application to the wearer's face.

Central window 12 has a base rim or perimeter region 20 which is attached to base 14 by, for instance, being integrally formed with base 14 or sealed thereto within a groove 21. Central window 12 may be oblong, e.g., oval, or round in shape, and preferably is made of a transparent material that enables the wearer to see therethrough. The material may be a clear plastic or polycarbonite. The plastic can be a rigid plastic, a flexible plastic or a plastic film, such as Handi-Wrap™ plastic film sold by DowBrands L.P. located in Indianapolis, Ind. In the preferred embodiment, central window 12 is designed with a span or diameter of approximately one to two inches. The material should be impermeable to the passage of water vapor therethrough to ensure moisture does not escape from the wearer's eye.

Collar 17 can be integrally formed with base 14, or it can be a separate layer having a front surface 22 connected with base 14 and a back surface 24 for receiving adhesive 18. Preferably, collar 17 extends radially outward from base 14 and is made of a flexible material. Specifically, the material for the collar 17 can be an impermeable or semi-permeable plastic, cloth or tape, such as SURGICAL PAPER TAPE™, distributed by 3M Corporation, Elastoplast, or Flexzan™, distributed by Dow Hickman Co. For most applications, however, both base 14 and collar 17 should be made of a material that is impermeable to the passage of water vapor therethrough. Thus, central window 12 in combination with base 14 and collar 17 provide a barrier that restricts the ingress of bacteria to the eye and the egress of moisture from the eye. When removable backing 19 is peeled from adhesive 18, collar 17 and adhesive 18 are pressed against a face 26 of a wearer about an eye 28 of the wearer to form a sealed cavity 30 over eye 28.

Figure 3:
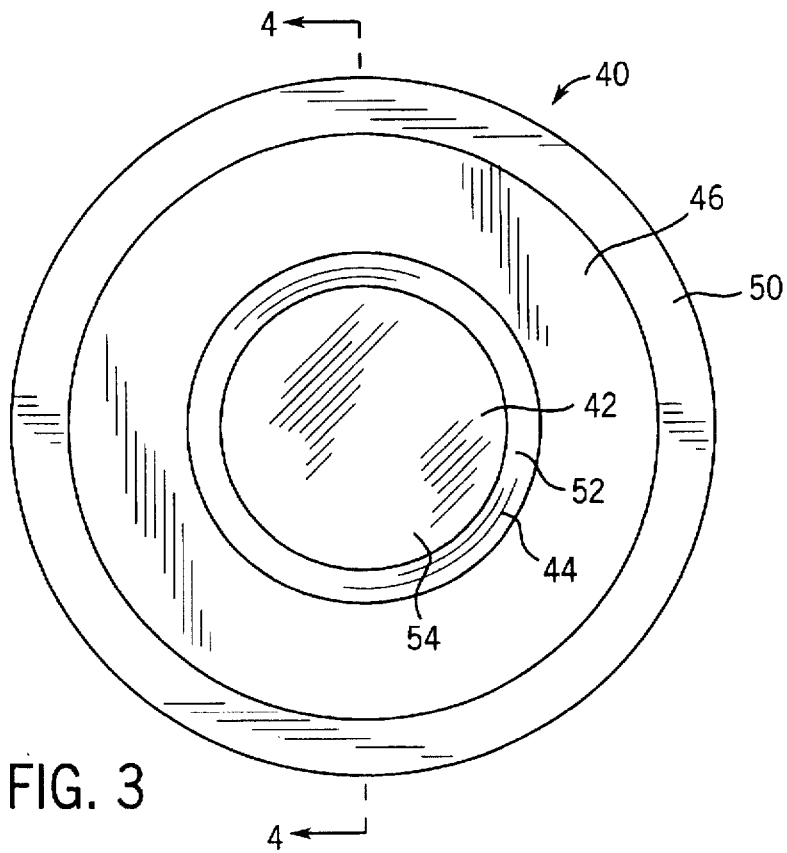
FIG. 3 is an alternate embodiment of the membrane shield illustrated in FIG. 1.
Figure 4:
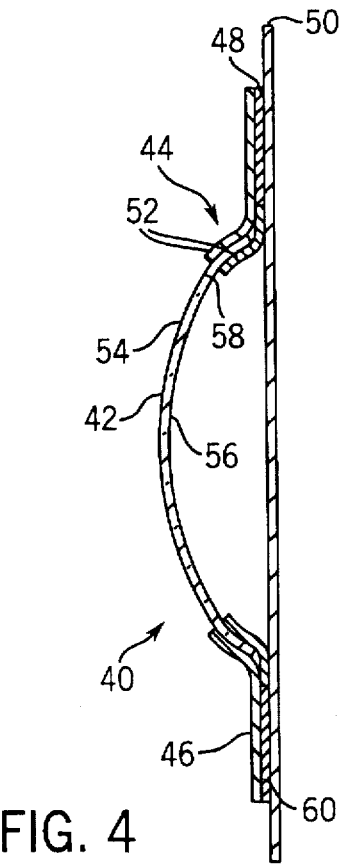
FIG. 4 is a cross sectional view taken generally along line 4—4 of FIG. 3

Referring generally to FIGS. 3 and 4, an alternate embodiment of the invention is illustrated. A membrane shield 40, according to an alternate embodiment of the invention, includes a window 42, a base region 44, a collar 46, an adhesive layer 48 and a backing layer 50.

As described above, window 42 can be formed from a variety of materials, but is preferably formed from a moisture impermeable transparent material. For example, window 42 can be formed from rigid plastic, flexible plastic or plastic film. In the embodiment illustrated, base region 44 includes a pair of flexible flaps 52 with one flap adhered to an outer surface 54 of window 42 and the other flap adhered to an inner surface 56 of window 42. Thus, a perimeter region 58 of window 42 is sealed between flexible flaps 52.

Collar 46 is also preferably a flexible material that extends radially outwardly from perimeter region 58 and base region 44. In the illustrated embodiment, collar 46 is integrally formed with one of the flexible flaps 52, such as the flexible flap adhered to outer surface 54 of window 42. Collar 46 and base region 44 can be formed of a variety of materials that are impermeable to the passage of water vapor. For example, a variety of plastics or paper materials could be used. However, with paper materials, it often is necessary to use paper coated with wax, polypropylene or polyethylene to insure that it is impermeable to the passage of moisture.

Adhesive layer 48 is disposed on a contact surface 60 of collar 46 that would be disposed adjacent the wearer's face when membrane shield 40 is adhered about a wearer's eye. Adhesive layer 48 is preferably a hypoallergenic adhesive that can be applied against the skin of a mammalian wearer. In some applications, it is preferred that the adhesive layer 48 comprise a gel, either alone or combined with a conventional adhesive, such as that used on surgical tape. For example, the gel could be applied to a radially inner portion of collar 46, and the conventional adhesive could be applied to a radially outer portion of the collar. One exemplary adhesive layer is petroleum jelly which provides both adhesion and a water vapor impermeable boundary between membrane shield 40 and the face of the wearer.

Furthermore, in many applications it is preferred that central window 12 or window 42 be formed as a lens. Window 42, for example, can be contoured as a lens to improve the vision of the wearer, as conventionally done with corrective glasses. If, for instance, the wearer normally requires reading glasses, eye shields without lenses might prohibit the wearer from reading during the evening. However, central window 12 or window 42 can readily be fashioned to correct vision disorders, such as farsightedness or nearsightedness. Also, as with normal corrective glasses, central window 12 and window 42 can be formed as bifocal lenses.

It will be understood that the foregoing description is of preferred exemplary embodiments of this invention and that the invention is not limited to the specific form shown. For example, the window and collar can be made in a variety of shapes, sizes and contoured configurations to facilitate ease of use by the wearer. The collar, for instance, can be round, oblong or have protruding flaps to promote adhesion to the wearer's face. The base can be rigid or flexible and can include one or two flaps adhered to the perimeter region of the window. Additionally, the impermeability of the collar can arise from the use of an impermeable adhesive layer rather than an impermeable collar material. These and other modifications may be made in design and arrangement of the elements without departing from the scope of the invention as expressed in the appended claims.

What is claimed is:

1. A moisture shield for application to a mammalian face to retain moisture in a mammalian eye, comprising:
   a window having a perimeter region, wherein the window comprises a lens;
   a base to which the perimeter region is sealingly attached, the base adjoining a flexible collar extending outwardly from the perimeter region and being impermeable to the passage of water vapor therethrough; and
   an adhesive layer disposed on the flexible collar to permit attachment of the moisture shield to the mammalian face about the mammalian eye.

2. The moisture shield as recited in claim 1, further comprising a removable backing layer adhered to the adhesive layer.

3. The moisture shield as recited in claim 1, wherein the base includes a flexible plastic material.

4. The moisture shield as recited in claim 3, wherein the adhesive layer includes a gel.

5. The moisture shield as recited in claim 4, wherein the gel is petroleum jelly.

6. The moisture shield as recited in claim 3, wherein the window is a transparent plastic material.

7. The moisture shield as recited in claim 6, wherein the lens is contoured to correct for farsightedness.

8. The moisture shield as recited in claim 6, wherein the transparent plastic material is a rigid material.

9. The moisture shield as recited in claim 6, wherein the window is oblong.

10. A moisture shield for application to a mammalian face to retain moisture in a mammalian eye, comprising:
    a window having a perimeter region, wherein the window comprises a flexible material;
    a base attached to the perimeter region;
    a collar attached to the base, the collar including a contact surface; and an adhesive layer applied to the contact surface to permit the moisture shield to be attached to the mammalian face about the mammalian eye; wherein the window, the base and the collar are impermeable to moisture from the mammalian eye.

11. The moisture shield as recited in claim 10, wherein the window is a transparent material.

12. The moisture shield as recited in claim 11, further comprising a removable backing layer adhered to the adhesive layer.

13. The moisture shield as recited in claim 10, wherein the adhesive layer comprises a gel.

14. The moisture shield as recited in claim 13, wherein the gel comprises petroleum jelly.

15. The moisture shield as recited in claim 10, wherein the flexible material comprises a plastic film.

16. A method for making a moisture shield to cover an eye of a mammal comprising the steps of:

forming a window;

combining a collar with the window, such that the collar extends outwardly from the window; and applying a gel to the collar to permit adhering the collar to the mammal about the eye.

17. The method as recited in claim 16, wherein the step of forming includes the step of forming a moisture impermeable window and the step of combining includes the step of combining a moisture impermeable collar with the moisture impermeable window.

18. The method as recited in claim 16, wherein the step of applying includes the step of applying petroleum jelly to the collar.

19. The method as recited in claim 16, wherein the step of forming includes forming a flexible plastic window.

20. The method as recited in claim 16, wherein the step of forming includes the step of forming the window as a lens.

* * * * *